United States Patent [19]

Sestanj et al.

[11] Patent Number: 4,499,310

[45] Date of Patent: Feb. 12, 1985

[54] 5-METHYL-1-(TRIFLUOROMETHYL)-2-NAPHTHALENOL, PROCESS FOR ITS PREPARATION AND ETHERS THEREOF

[75] Inventors: Kazimir Sestanj, St. Laurent; Steven Fung, Montreal; Nedumparambil A. Abraham, Ormeaux; Francesco Bellini, Mount Royal, all of Canada

[73] Assignee: Ayerst, McKenna & Harrison, Inc., Montreal, Canada

[21] Appl. No.: 506,740

[22] Filed: Jun. 22, 1983

Related U.S. Application Data

[62] Division of Ser. No. 321,302, Nov. 13, 1981, Pat. No. 4,408,077.

[51] Int. Cl.³ .................. C07C 39/14; C07C 37/06; C07C 43/20
[52] U.S. Cl. ................................ 568/634; 568/737
[58] Field of Search .......................... 568/634, 737

[56] References Cited

U.S. PATENT DOCUMENTS 4,408,077 10/1983 Sestanj et al. .................. 568/441

OTHER PUBLICATIONS

Harvey et al., Jour. Chem. Soc., (1930), 423–431.

*Primary Examiner*—Bernard Helfin
*Attorney, Agent, or Firm*—Arthur E. Wilfond

[57] ABSTRACT

A process and intermediates for preparing 6-(lower alkoxy)-5-(trifluoromethyl)-1-naphthalenecarboxylic acid derivatives are disclosed. The derivatives are useful for preparing aldose reductase inhibitors. With reference to the process, 1,1,1-trifluoro-5-(2-methylphenyl)-2,3-pentadione 3-oxime is cyclized to give a key intermediate 3,4-dihydro-1-hydroxy-5-methyl-1-(trifluoromethyl)-2(1H)-naphthalenone oxime; and 3,4-dihydro-1-hydroxy-5-methyl-1-(trifluoromethyl)-2(1H)-naphthalenone is aromatized to 5-methyl-1-(trifluoromethyl)-2-naphthalenol with a dehydrating agent.

3 Claims, No Drawings

5-METHYL-1-(TRIFLUOROMETHYL)-2-NAPHTHALENOL, PROCESS FOR ITS PREPARATION AND ETHERS THEREOF

This is a division of application Ser. No. 321,302, filed Nov. 13, 1981, now U.S. Pat. No. 4,408,077.

This invention concerns a new process and intermediates for preparing 6-(lower alkoxy)-5-(trifluoromethyl)-1-naphthalenecarboxylic acid.

BACKGROUND OF THE INVENTION 6-(Lower alkoxy)-5-(trifluoromethyl)-1-naphthalenecarboxylic acid is a key intermediate for preparing N-[[6-(lower alkoxy)-5-(trifluoromethyl)-1-naphthalenyl]thioxomethyl]-N-(lower alkyl)glycine derivatives of the formula

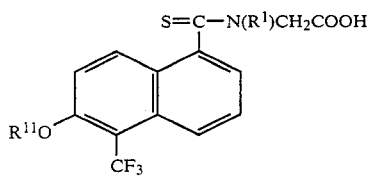

in which $R^I$ and $R^{II}$ are the same or different lower alkyls. The latter derivatives are aldose reductase inhibitors and are useful for treating diabetic complications; for example, neuropathy, nephropathy, retinopathy, cataracts and atherosclerosis.

A process for preparing the key intermediate, the transformation of the intermediate to the aldose reductase inhibitors and the use of the inhibitors for treating diabetic complications are described in copending U.S. patent application Ser. No. 321,306, now U.S. Pat. No. 4,439,617 of K. Sestanj et al., filed on the same data hereas, the pertinent portions of which are herein incorporated by reference.

The process for the key intermediate in the copending application is exemplified as follows: 6-methoxy-1-naphthalenecarboxylic acid methyl ester is reacted with iodine and iodic acid in the presence of 98% sulfuric acid to give 5-iodo-6-methoxy-1-naphthalenecarboxylic acid methyl ester, which in turn is reacted with trifluoromethyl iodide and copper powder in a stainless steel autoclave to give 6-methoxy-5-(trifluoromethyl)-1-naphthalenecarboxylic acid methyl ester. Hydrolysis of the latter compound with dilute aqueous sodium hydroxide gives 6-methoxy-5-(trifluoromethyl)-1-naphthalenecarboxylic acid, one of the key intermediate noted hereinbefore. The latter compound also can be named 5-(trifluoromethyl)-6-methoxy-1-naphthalenecarboxylic acid.

Our novel process for preparing the key intermediate, although having more steps, is more efficient and less expensive than the process exemplified in the previous paragraph. More explicitly, the present process allows at least a doubling of the yield of the key intermediate. Furthermore, the process allows at least a ten-fold reduction in the cost of preparing the intermediate; a major contributing factor to the cost reduction being the use of trifluoroacetic acid, an inexpensive source for the trifluoromethyl group, rather than trifluoromethyl iodide, an expensive and more noxious reagent. Still furthermore, the present process does away with the need for high pressure equipment. All these advantages serve to make the present process a much more attractive commercial process than the process of the copending application.

The transformation of the key intermediate to the aldose reductase inhibitors, as disclosed in the copending application, is accomplished by coupling an activated ester of the key intermediate with the appropriate glycine ester to obtain the corresponding N-[(1-naphthalenyl)carbonyl]glycine ester; reacting the latter compound with phosphorus pentasulfide to obtain the corresponding N[(1-naphthalenyl)thioxomethyl]glycine ester; and then hydrolyzing the lastnamed compound to obtain the desired N-[[6-(lower alkoxy)-5-(trifluoromethyl)-1-naphthalenyl]thioxomethyl]-N-(lower alkyl)glycine. Optionally, the order of the last two steps can be reversed.

SUMMARY OF THE INVENTION

A new process for preparing 6-(lower alkoxy)-5-(trifluoromethyl)-1-naphthalenecarboxylic acid is realized by:

(a) reacting the Grignard reagent of 2-(3-halopropyl)-1-methylbenzene with trifluoroacetic acid, lithium trifluoroacetate or $CF_3COOMg$-(halide) to obtain 1,1,1-trifluoro-5-(2-methylphenyl)-2-pentanone;

(b) reacting the 1,1,1-trifluoro-5-(2-methylphenyl)-2-pentanone with an alkali metal nitrite or lower alkyl nitrite in the presence of an acid to obtain 1,1,1-trifluoro-5-(2-methylphenyl)-2,3-pentanedione 3-oxime;

(c) cyclizing the 1,1,1-trifluoro-5-(2-methylphenyl)-2,3-pentanedione 3-oxime with 100% sulfuric acid or with aqueous sulfuric acid containing from 50 up to 100% by weight of sulfuric acid per volume of water, i.e. 50% up to 100% (w/v) aqueous sulfuric acid, to obtain 3,4-dihydro-1-hydroxy-5-methyl-1-(trifluoromethyl)-2(1H)-naphthalenone oxime;

(d) hydrolyzing the 3,4-dihydro-1-hydroxy-5-methyl-1-(trifluoromethyl)-2(1H)-naphthalenone oxime in the presence of an acid to obtain 3,4-dihydro-1-hydroxy-5-methyl-1-(trifluoromethyl)-2(1H)-naphthalenone;

(e) aromatizing the 3,4-dihydro-1-hydroxy-5-methyl-1-(trifluoromethyl)-2(1H)-naphthalenone with a dehydrating agent of the type capable of acylating tertiary alkanols to obtain 5-methyl-1-(trifluoromethyl)-2-naphthalenol;

(f) O-(lower)alkylating the 5-methyl-1(trifluoromethyl)-2-naphthalenol under anhydrous conditions with an O-(lower)alkylating agent to obtain 2-(lower alkoxy)-5-methyl-1-(trifluoromethyl)naphthalene; and (g) transforming the 2-(lower alkoxy)-5-methyl-1-(trifluoromethyl)-naphthalene to 6-(lower alkoxy)-5-(trifluoromethyl)-1-naphthalenecarboxylic acid.

The 2-(lower alkoxy)-5-methyl-1-(trifluoromethyl)-naphthalene can be transformed to 6-(lower alkoxy)-5-(trifluoromethyl)-1-naphthalenecarboxylic acid by oxidizing the 2-(lower alkoxy)-5-methyl-1-(trifluoromethyl)naphthalene with potassium permanganate; or by halogenating the 2-(lower alkoxy)-5-methyl-1-(trifluoromethyl)naphthalene with a halogenating agent capable of converting a methylnaphthalene to a (halomethyl)naphthalene to obtain 5-(halomethyl)-2-(lower alkoxy)-1-(trifluoromethyl)naphthalene, subjecting the latter compound to the Sommelet reaction to obtain 6-(lower alkoxy)-5-(trifluoromethyl)-1-naphthalenecarboxaldehyde and oxidizing the latter compound with a reagent capable of converting a naphthalenecarboxaldehyde to a naphthalenecarboxylic acid.

With reference to the process, the novel intermediate 3,4-dihydro-1-hydroxy-5-methyl-1-(trifluoromethyl)-2(1H)-naphthaleneone oxime, and its preparation of a novel cyclization of 1,1,1-trifluoro-5-(2-methylphenyl)-2,3-pentanedione 3-oxime with sulfuric acid, is disclosed.

Again with reference to the process, the novel intermediate 5-methyl-1-(trifluoromethyl)-2-naphthalenol, and its preparation by a novel aromatization of 3,4-dihydro-1-hydroxy-5-methyl-1-(trifluoromethyl)-2-(1H)-naphthaleneone with a dehydrating agent of the type capable of acylating tertiary alkanols, is disclosed.

DETAILED DESCRIPTION OF THE INVENTION

The term "lower alkyl" as used herein means a straight chain alkyl radical containing from one to six carbon atoms, preferably one to three carbon atoms, or a branched chain alkyl radical containing three or four carbon atoms and includes methyl, ethyl, propyl, 1-methylethyl, propyl, 2-methylpropyl and 1,1-dimethylethyl.

The term "lower alkoxy" as used herein means a straight chain alkoxy radical containing from one to six carbon atoms, preferably one to three carbon atoms, or a branched chain alkoxy radical containing three or four carbon atoms and includes methoxy, ethoxy, 1-methylethoxy, butoxy and hexoxy.

The term "halo" or "halide" as used herein means a halo radical or halide selected from the group consisting of bromine, chlorine and iodine.

The term "lower alkanol" as used herein means both straight and branched chain alkanols containing from one to four carbon atoms and includes methanol, ethanol, isopropanol and butanol.

The term "organic proton acceptor" as used herein means the organic bases or amines, for instance, triethylamine, pyridine, N-ethylmorpholine, 4-(dimethylamino)pyridine and 1,5-diazabicyclo[4.3.0]non-4-ene.

The term "inorganic proton acceptor" as used herein means the inorganic bases, preferably the alkali metal hydrides, hydroxides and carbonates, or their corresponding lower alkoxides, for example, sodium hydride, potassium hydroxide, sodium carbonate, potassium carbonate and sodium ethoxide.

The term "proton acceptor" as used herein means a proton acceptor selected from an organic proton acceptor and inorganic proton acceptor, as defined hereinabove.

The process of this invention is illustrated by the following reaction scheme in which R is lower alkoxy and X is halo:

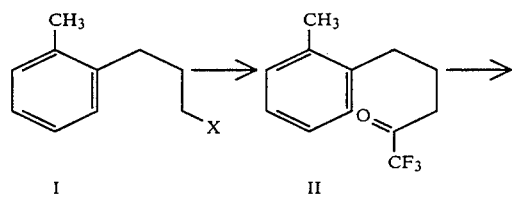

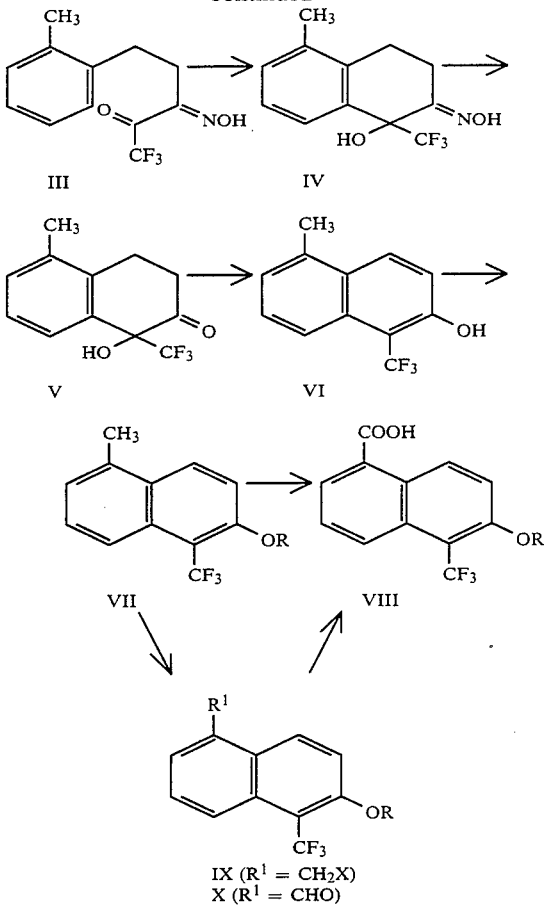

The requisite starting material of formula I, is either known or can be prepared by known methods. For example, 1-(3-bromopropyl)-2-methylbenzene is described by J. Harvey et al., J. Chem. Soc., 423 (1930). Two other procedures for preparing the starting materials are exemplified herein in example 1.

Referring to the reaction scheme, the starting material of formula I, a 1-(3-halopropyl)-2-methylbenzene, is reacted with about oe molar equivalent of magnesium to obtain its corresponding Grignard reagent. In turn, the Grignard reagent is reacted with a trifluoroacetyloxy derivative, e.g. trifluoroacetic acid, lithium trifluoroacetate or $CF_3COOMg$-(halide), to obtain 1,1,1-trifluoro-5-(2-methylphenyl)-2-pentanone, the α-trifluoromethylketone of formula II. Convenient and practical conditions for the Grignard reaction include the use of at least two molar equivalents, preferably 2.1 to 2.4 molar equivalents, of the Grignard reagent when employing trifluoroacetic acid, or using at least one molar equivalent, preferably 1.1 to 1.3 molar equivalents of the Grignard reagent when employing lithium trifluoroacetic or $CF_3COOMg$-(halide). It is more economical to use the latter two reactants instead of trifluoroacetic acid, the reason being that the active hydrogen of trifluoroacetatic acid wastefully consumes one molar equivalent of the valuable Grignard reagent. Suitable solvents for the formation of the Grignard reagent and the subsequent Grignard reaction are diethyl ether or diisopropyl ether. The Grignard reagent formation is performed usually at temperatures ranging from 25° to 80° C., or at the reflux temperature of the solvent until virtually all the magnesium is dissolved. The Grignard reaction is performed usually at initial temperatures ranging from −75° to 5° C. with subsequent warming of the reaction mixture to 25° C. over a period of one to 24 hours.

In a preferred embodiment, the 1-(3-halopropyl)-2-methylbenzene is reacted with one molar equivalent of magnesium in refluxing diethyl ether containing a crystal of iodine until the magnesium is consumed. The Grignard reagent, so obtained, is reacted with 1.2 to 1.3 molar equivalents of lithium trifluoroacetate in diethyl ether at an initial temperature of about −75° C. to −50° C., followed by gradual warming of the reaction mixture to room temperature (25° C.) over a period of eight to 18 hours. The product, the $\alpha$-trifluoromethylketone of formula II, thereafter is isolated by extraction and purified by distillation under reduced pressure.

The $\alpha$-trifluoromethylketone of formula II is transformed into its corresponding $\alpha$-oximinoketone of formula III by reaction with an alkali metal nitrite, for instance, sodium nitrite or potassium nitrite, or by reaction with a lower alkyl nitrite, for instance, methyl nitrite or amyl nitrite. Usually one to five molar equivalents of the alkali metal nitrite or lower alkyl nitrite is employed. The reaction is performed best in the presence of at least one molar equivalent of an acid. Any of the usual organic or inorganic acids can be employed advantageously for this reaction, for example, acetic acid, p-toluenesulfonic acid, hydrochloric acid, sulfuric acid, hydrobromic acid, hydroiodic acid, phosphoric acid or perchloric acid. The preferred acid for this reaction is acetic acid. A suitable solvent for this reaction is water, acetic acid or a mixture of water and acetic acid. The reaction is performed usually at temperatures ranging from 0° to 35° C. for a period of two to 24 hours.

In a preferred embodiment, the $\alpha$-trifluoromethylketone of formula II is reacted with three to five molar equivalents of potassium nitrite in a medium of equal parts by volume of water and acetic acid in the presence of an excess of isopropanol or tert-butanol. The reaction is performed at 20° to 35° C. for two to 24 hours. Thereafter, the reaction mixture is poured into water and the $\alpha$-oximinoketone of formula III is isolated by extraction. The $\alpha$-oximinoketone is pure enough for the next step; however, it may be purified further by recrystallization from hexane.

In the next step, the $\alpha$-oximinoketone of formula III is cyclized with sulfuric acid to give the bicyclic oxime of formula IV. The reaction is performed best by employing a large excess of 100% sulfuric acid (including fuming sulfuric acid) or by employing sulfuric acid which has been diluted with up to 50% by weight/volume of water. Throughout this application, the percentages for mixtures of acids and water are based on the relationship of the weight of the acid to the volume of water. Aqueous sulfuric acid (80 to 98%, w/v) is preferred. Commercial sulfuric acid, containing 93 to 98% w/v of sulfuric acid in water, has been found to be a very practical reagent. The sulfuric acid, or the aqueous solution of sulfuric acid, acts as a suspending agent during the initial part of the reaction. Practical temperatures and times for the reaction range from 15° to 40° C. and from 30 minutes to two hours. The completion of the reaction can usually be judged by the complete solution of the starting material. The reaction can be performed with or without an inert organic solvent, for example, benzene, toluene or m-xylene.

In a preferred embodiment, the $\alpha$-oximinoketone of formula III is suspended at 0° C. in toluene and about 10 to 20 molar equivalents of concentrated sulfuric acid (93 to 98% w/v of sulfuric acid in water) is added to the suspension. The ratio of toluene to sulfuric acid is about four to three by volume. The resulting suspension is stirred and allowed to warm to 20° to 30° C. After about 30 minutes the reaction is complete. Thereafter, the reaction mixture is poured into cold water or onto ice and the bicyclic oxime of formula IV is isolated by extraction with diethyl ether.

Concerning the last step, the choice of sulfuric acid as the agent for this cyclization is important. The use of other mineral acids, for example, hydrochloric acid, leads to an inferior product containing several contaminants such as undesirable aromatic and ketonic products. In fact, the splendid yield of the pure bicyclic oxime of formula IV, under the above described conditions, is somewhat surprising. The conditions employed are dehydrating conditions which would ordinarily be expected to cause the bicyclic oxime to undergo aromatization as it is formed (cf. the aromatization reaction described below).

Turning to the next step, the bicyclic oxime of formula IV if hydrolyzed in the presence of water with an organic or inorganic acid into the corresponding bicyclic ketone of formula V. Suitable acids, for example, are hydrochloric acid, sulfuric acid, phosphoric acid, trifluoroacetic acid or p-toluenesulfuric acid. The use of a strong mineral acid, for instance, hydrochloric acid, sulfuric acid or phosphoric acid is preferred. Suitable solvents include water, the lower alkanols and acetic acid. The reaction mixture is maintained at a temperature ranging from 0° to 100° C. or at the reflux temperature of the solvent employed until hydrolysis is complete, usually from one to eight hours.

In a preferred embodiment, the hydrolysis is accomplished by bringing the bicyclic oxime into contact with an excess of concentrated hydrochloric acid (33 to 38% by weight/volume hydrogen chloride in water) at 0° to 10° C. and stirring the reaction mixture for one to four hours at 10° to 80° C.

In the next step of the process, the bicyclic ketone of formula V is aromatized with a dehydrating agent to give the naphthenol of formula VI. The dehydrating agent employed is the type which also can be classed as an acylating agent capable of acylating a tertiary alkanol. In other words, the dehydrating agent is one which ordinarily is capable of acylating a tertiary alcohol to give a suitable leaving group which can be eliminated in concert with a neighboring hydrogen thereby effecting a dehydration. Suitable dehydrating agents of this type are exemplified by thionyl chloride, thionyl bromide, phosphorus oxychloride, acetyl chloride, mesyl chloride or acetyl chloride. The latter agents usually are employed in the presence of an organic proton acceptor. Trifluoroacetic anhydride and acetic anhydride are still other examples of this type of dehydrating agent. Preferred dehydrating agents are thionyl chloride, thionyl bromide, phosphorus oxychloride and trifluoroacetic anhydride. A dehydrating agent which is capable of providing a better leaving group is the better dehydrating agent.

Generally, the aromatization is conducted under anhydrous conditions using at least one molar equivalent, usually 1.2 to 2.0 molar equivalents, of the dehydrating agent. Practical and convenient reaction temperatures and times range from −10° to 50° C. for a period of ten minutes to two hours, or until the reaction is complete as judged by thin layer chromatography (tlc).

In a preferred embodiment, the bicyclic ketone of formula V is brought into contact at 0° to 20° C. under anhydrous conditions with 1.2 to 1.5 molar equivalents of thionyl chloride in the presence of a suitable proton acceptor, preferably pyridine. In practice, it has been found that the use of a molar equivalent of the proton acceptor is sufficient for good results. The addition of a catalytic amount of a strong base, for example, 4-(dimethylamino)pyridine, to this reaction mixture has been found to enhance the yield of the desired product. The reaction is complete in about 30 to 60 minutes as judged by tlc. Thereafter, the reaction mixture is decomposed with water and the desired product is isolated by extraction with a non polar, water immiscible solvent, for example, hexane or diethyl ether.

The naphthalenol of formula VI now is reacted with an O-(lower)alkylating agent to give the corresponding lower alkyl ether of formula VII. The reaction is best performed in an inert organic solvent under anhydrous conditions using 1.0 to 1.5 molar equivalents of the O-(lower)alkylating agent. Suitable inert organic solvents include dimethylformamide, tetrahydrofuran, acetone and toluene. Suitable O-(lower)alkylating reagents include the di(lower)alkyl sulfates or lower alkyl halides. The reaction is performed advantageously in the presence of an inorganic or organic acceptor. The amount of the proton acceptor generally used is at least equivalent to the amount of the naphthalenol employed. Suitable proton acceptors include sodium carbonate, potassium carbonate and triethylamine. It is advantageous to avoid strongly basic conditions when performing this reaction. Although the optimum temperature and reaction time will vary depending on the reactants employed, the reaction usually is performed at 20° to 80° C., or at the boiling point of the reaction mixture, for 30 minutes to 24 hours.

In a preferred embodiment, 1.2 to 1.5 molar equivalents of the appropriate di(lower)akyl sulfate (e.g. dimethyl sulfate or diethyl sulfate) in the presence of 1.2 to 2.5 molar equivalents of potassium carbonate is reacted with the napthalenol of formula VI in dimethylformamide for one to two hours at 20° to 30° C. In this manner, the corresponding lower alkyl ether (e.g. the methyl or ethyl ether) of formula VII is obtained.

In the next step, the lower alkyl ether of formula VII is oxidized to the corresponding carboxylic acid of formula VIII, the key intermediate noted above. Potassium permanganate is the oxidizing agent of choice. The reaction is conducted best with four to eight molar equivalents of potassium permanganate in an inert solvent, for instance water or a mixture of water and tert-butanol. Practical temperature and times for this reaction are 20° to 120° C. and two to eight hours, respectively.

In a preferred embodiment, the oxidation is effected at 80° to 100° C. with 4.8 to 5.2 molar equivalents of potassium permanganate in a mixture of one part by volume of water and one to three parts by volume of tert-butanol for six to eight hours.

Alternatively and preferably, the conversion of the lower alkyl ether of formula VII to the carboxylic acid of formula VIII is realized in a better yield by a process involving the Sommelet reaction. More specifically, the lower alkyl ether of formula VII is converted to its corresponding halomethyl analog of formula IX with a suitable halogenating agent capable of converting a methylnaphthalene to a (halomethyl)naphthalene. Suitable halogenating agents include the halogens, N-halosuccinimides, 1,3-dihalo-5,5-dimethylhydantoins or N-haloacetamides, for example, chlorine, N-bromosuccinimide, N-chlorosuccinimide, N-iodosuccinimide, 1,3-dibromo-5,5-dimethylhydantoin or N-bromosuccinimide. About 1.0 to 1.2 molar equivalents of the halogenating agent is employed in an inert organic solvent, for instance, carbon tetrachloride. Reaction times and temperatures are not critical but depend on the nature of the reactants. Practical times and temperatures for the halogenation range from ten minutes to four hours at 20° to 80° C. It is advantageous to use a catalyst, for example benzoyl peroxide or a high intensity light, to promote the halogenation.

In a preferred embodiment, the halogenation is done with 1.2 to 1.5 molar equivalents of N-bromosuccinimide or N-chlorosuccinimide in boiling carbon tetrachloride to obtain the corresponding halomethyl analog of formula IX in which X is bromo or chloro, respectively.

The halomethyl analog of formula IX, so obtained, is reacted with hexamethylenetetramine to give the corresponding heximinum salt. The salt is hydrolyzed with an acid to give 6-(lower alkoxy)-5-(trifluoromethyl)-1-naphthalenecarboxaldehyde (X). The conditions used are those of the Sommelet reaction. See, for example, M. S. Newman and W. M. Hung, Org. Prep. and Proc. Int., 4, 227 (1972), S. J. Angyal, Organic Reactions, 8, 197 (1954) and S. J. Angyal et al., Organic Syntheses, 30, 67 (1950).

In a preferred embodiment, the halomethyl analog of formula IX is reacted with 1.5 to 3 molar equivalents of hexamethylenetetramine at temperatures ranging from 50° to 120° C. in an inert solvent, preferably a mixture of one to one parts by volume of acetic acid and water, for one to four hours. The resulting intermediate heximinium salt, while still in the reaction mixture, is hydrolyzed by the addition to the reaction mixture of a strong mineral acid, for instance, hydrochloric acid or sulfuric acid, to give 6-(lower alkoxy)-5-(trifluoromethyl)-1-naphthalenecarboxaldehyde (X).

Thereafter, the latter compound is oxidized with a reagent capable of oxidizing a napthalenecarboxaldehyde to a naphthalenecarboxylic acid. Although a variety of suitable oxidizing agents can be used for this purpose, for example, potassium permanganate, chromic acid in sulfuric acid (Jone's reagent), hydrogen peroxide or silver oxide, it has been found that potassium permanganate is a very efficient and practical oxidizing agent. In a preferred embodiment, 6-(lower alkoxy)-5-(trifluoromethyl)-1-naphthalenecarboxaldehyde is oxidized with 1.5 to 2.0 molar equivalents of potassium permanganate, under the conditions described for the previous oxidation to give the key intermediate, 6-(lower alkoxy)-5-(trifluoromethyl)-1-naphthalenecarboxylic acid.

The following examples illustrate further this invention.

EXAMPLE 1

1-(3-Chloropropyl)-2-methylbenzene (I, X=Cl)

Procedure A:

To a stirred solution of 1-methyl-2-(2-propenyl)-benzene (134.6 g, 1.02 mol), described by C. D. Hurd and H. T. Bollman, J. Amer. Chem. Soc., 56, 447 (1934), in dry tetrahydrofuran (THF, 300 mL) under nitrogen, 1M $BH_3 \cdot THF$ in THF (400 mL, 0.40 mol) was added at 0° C.

The reaction mixture was stirred at 0° C. for 30 min and at room temperature (25° C.) until the reaction was complete (40 min). Thereafter, the reaction mixture was cooled to 0° C and 3N aqueous NaOH (133 mL, 0.40 mol) was added carefully to the mixture, followed by the dropwise addition of 30% $H_2O_2$ (133 mL, 1.18 mol). The reaction mixture was stirred for 18 hr at room temperature and then extracted with diethyl ether (2×). The diethyl ether extract was washed successively with water, a saturated aqueous solution of $NaHCO_3$, 10% aqueous $NaHSO_3$ solution (3×), water and brine. The extract was dried ($MgSO_4$) and concentrated under reduced pressure to give 2-methyl-benzenepropanol (139.2 g, 91% yield; nmr ($CDCl_3$) δ 1.8 (m, 2H), 2.3 (s, 3H), 2.7 (t, J=7 Hz, 2H), 3.65 (t, J=7 Hz, 2H), 7.1 (s, 4H). 2-Methyl-benzenepropanol has been described previously by J. Harvey et al., J. Chem. Soc., 423 (1930).

The latter compound (60.0 g, 0.40 mol) was placed in a reaction flask and cooled to 0° C. Thionyl chloride (53.3 g, 0.44 mol) was added dropwise to the stirred compound at 0° C. under nitrogen. Thereafter, the mixture was stirred for 18 hr at room temperature. Excess thionyl chloride was removed by distillation under reduced pressure. Distillation of the residue gave the title compound (44.5 g, 66% yield); bp 62°–64° C./0.25 mm; nmr ($CDCl_3$) δ 2.0 (q, J=7 Hz, 2H), 2.3 (s, 3H), 2.75 (t, J=7 Hz, 2H), 3.5 (t, J=7 Hz, 2H), 7.1 (s, 4H).

Procedure B:

A mixture of freshly distilled 1-chloro-2-methylbenzene (94.9 g, 0.75 mol), magnesium turnings (18.23 g, 0.75 gram atom) and a crystal of iodine was placed in a 1 L, round bottomed, 3-necked flask equipped with a reflux condenser, dropping funnel, thermometer and stirrer. The mixture was protected from atmospheric moisture by means of a $CaCl_2$ tube at the top of the condenser. Dry THF (336 mL) was placed in the dropping funnel. The flask was then placed in an oil bath having a temperature of 145° C. THF (3 ml) was added to the mixture. The reaction started within an half hour as indicated by the disappearance of the purple color of the iodine and the development of a light brown color. The internal temperature began to rise above 145° C. THF was added. Thereafter, the internal temperature of the reaction mixture was not allowed to rise above 145° C. by the controlled addition of THF. As the reaction proceeded, the rate of addition of THF was increased and the bath temperature cooled to 120° C. All the THF was added within 2 hr. The mixture was stirred for another 2 hr at an oil bath temperature of 120° C. The internal temperature was 76° C. after this period and most of the magnesium turnings has dissolved.

The flask containing the formed Grignard reagent was cooled in an ice bath. Under anhydrous conditions, the Grignard solution was siphoned into a 3-necked flask containing a dry ice-acetone cooled mixture of distilled 1-bromo-3-chloropropane (94.4 g, 0.6 mol) and a THF solution (18 mL) of $Li_2CuCl_4$ in THF (210 mL); see M. Tamura and J. Kochi, Synthesis, 3, 303 (1971). The $Li_2CuCl_4$ solution had been prepared by dissolving anhydrous $LiCl_2$ (0.2 mol) and anhydrous $CuCl_2$ (0.1 mol, obtained by heating $CuCl \cdot H_2O$ under reduced pressure at 110° C. for 18 hr) in THF (1 L).

The cooled mixture of the Grignard reagent, 1-bromo-3-chloropropane and $Li_2CuCl_4$ was allowed to come to room temperature over a period of 18 hr. The mixure was recooled in an ice-bath, and $NH_4Cl$ (30 g) in 90 mL of $H_2O$ and diethyl ether (1 L) were serially to the mixture. The supernatant layer of the mixture was separated from the solid residue of magnesium salt. The layer was washed (3×) with aqueous NaCl, dried ($Na_2SO_4$) and evaporated to dryness to give an oily residue (98.0 g). The magnesium salt residue was dissolved in 2N aqueous HCl. The resulting solution was extracted with diethyl ether. The diethyl ether extract was washed with aqueous NaCl, aqueous $NaHCO_3$, dried ($Na_2SO_4$) and evaporated to dryness to give a second oily residue (9.5 g). The two oily residues were combined and distilled under reduced pressure to given the title compound (91.1 g, 90% yield), identical with the compound obtained by Procedure A of this example.

EXAMPLE 2

1,1,1-Trifluoro-5-(2-methylphenyl-2-pentanone (II)

A solution of 1-3-(chloropropyl)-2-methylbenzene (88.1 g, 0.522 mol) in anhydrous diethyl ether (360 mL) was added dropwise over a period of 2 hr to magnesium turnings (12.6 g, 0.522 gram atom) and a crystal of iodine. The reaction mixture was heated at reflux and stirred during the addition. After completion of the addition, the mixture was heated at reflux for another 2 hr. The mixture was cooled and the clear supernatant solution was siphoned (under anhydrous conditions) into a stirred, dry ice-acetone cooled suspension of lithium trifluoroacetate (50 g, 0.417 mol) in diethyl ether (336 mL). The lithium trifluoroacetate can be prepared by the procedure described by G. W. Astrologes et al., J. Amer. Chem. Soc., 98, 2895 (1976). The mixture was stirred for 18 hr during which time the reaction mixture was allowed to come to room temperature. The reaction mixture was cooled in an ice bath. Crushed ice (300 mL) and 2N aqueous HCl (300 mL) were added to the reaction mixture. The ether layer was separated. The aqueous layer was extracted with diethyl ether (3×250 mL). The combined diethyl ether extract was washed successively with saturated NaCl and with aqueous $NaHCO_3$, dried ($Na_2SO_4$) and evaporated to dryness. The residue was distilled under reduced pressure to give 81.6 g (>85% yield) of the title compound; bp 68°–70° C./1.5 mm; nmr ($CDCl_3$) δ b 2.0 (m, 2H), 2.3 (s, 3H), 2.65 (m, 4H), 7.05 (s, 4H); ir ($CHCl_3$) $1760^{-1}$;uvλmax (MeOH) 271 nm (ε 250), 264 (300), 256 (250).

EXAMPLE 3

1,1,1-Trifluoro-5-(2-methylphenyl)-2,3-pentanedione 3-oxime (III)

A solution of potassium nitrite (22.2 g, 0.26 mol) in water (total volume=7.4 mL) was added in one portion to a stirred solution of 1,1,1-trifluoro-5-(2-methylphenyl-2pentanone (20 g, 0.087 mol), tert-butanol (25 mL) and acetic acid (25 mL) at 25° C. The reaction mixture was stirred at 25° C. for 2.5 hr. Another solution of potassium nitrite (7.5 g, 0.088 mol) in water (2.5 mL) then was added. After stirring for 1.5 hr, the reaction mixture was poured into water. The resulting mixture was extracted with diethyl ether (3×). The combined ether extracts were washed with water and then washed with a saturated aqueous solution of $NaHCO_3$. Thereafter, the organic extract was dried ($MgSO_4$) and concentrated under reduced pressure to give the title compound (22.1 g, 98% yield) as a yellow crystalline mass. This product was used for the reaction described in the following example. A sample of the product, recrystallized for hexane, had mp 80°-81° C.; nmr (CDCl$_3$) δ 2.35 (s, 3H), 2.8 (s, 4H), 7.1 (s, 4H); ir (CHCl$_3$) 3540, 3340, 1730, 1165$^{-1}$; Anal Calcd for C$_{12}$H$_{12}$F$_3$NO$_2$:C, 55.60% H, 4.67%; Found: C, 55.41% H, 4.60%.

EXAMPLE 4

3,4-Dihydro-1-hydroxy-5-methyl-1-(trifluoromethyl)-2-(1H)-naphthalenone oxime (IV)

Cold concentrated H$_2$SO$_4$ (12 ml, 98% w/v H$_2$SO$_4$ in water) was added to a stirred suspension of 1,1,1-trifluoro-5-(2-methylphenyl)-2,3-pentanedione 3-oxime (11.9 g, 45.9 mmol) in toluene (16 mL) at 0° C. The reaction mixture and allowed to warm to room temperature (25° C.) and then stirred for 30 min. Ice was added to the reaction mixture. The resulting mixture was extracted with diethyl ether (2×). The ether extract was washed successively with water and a saturated aqueous solution of NaHCO$_3$, dried (MgSO$_4$) and concentrated under reduced pressure to give the title compound (10.4 g, 87% yield). This product was used for the reaction described in the following example. A small sample was triturated with hexane to give off-white crystals; mp 154°-156° C.; nmr (CDCl$_3$) δ 2.3 (s, 3H), 2.9 (m, 4H), 7.2 (m, 2H), 7.6 (m, 1H); ir (CHCl$_3$) 3570, 3480, 1170 cm$^{-1}$; uvλmax (MeOH) 273 nm (ε 570), 266 (590).

EXAMPLE 5

3,4-Dihydro-1-hydroxy-5-methyl-1-(trifluoromethyl)-2(1H)-naphthalenone (V)

Concentrated HCl (460 ml, 38% w/v HCl in water) was added slowly to stirred 3,4-dihydro-1-hydroxy-5-methyl-1-(trifluoromethyl)-2(1H)-naphthalenone oxime (24.5 g, 94.4 mmol) at 0° C. The stirred mixture was heated to 70° C. and kept at that temperature for 2.5 hr. After being cooled to 25° C., the mixture was poured over 1 kg of ice. The resulting suspension was filtered. The collected solid was washed with water and dried to give the title compound (21.4 g, 93% yield). This product was used for the reaction described in the following example. A small sample of the product, recrystallized from hexane, had mp 122°-123° C.; nmr (CDCl$_3$) δ 2.3 (s, 3H), 3.1 (m, 4H), 7.2 (m, 2H), 7.55 (m, 1H); ir (CHCl$_3$) 3460, 1730, 1170, 1115 cm$^{-1}$; uvλmax (MeOH) 274 nm (ε 547), 267 (590); Anal Calcd for C$_{12}$H$_{11}$F$_3$O$_2$: C, 59.02% H, 4.54%; Found: C, 59.22% H, 4.44%.

EXAMPLE 6

5-Methyl-1-(trifluormethyl)-2-naphthalenol (VI)

Thionyl chloride (0.33 mL, 4.52 mmol) was added dropwise at about 5° C. to a stirred solution of 3,4-dihydro-1-hydroxy-5-methyl-1-(trifluoromethyl-2(1H)-naphthalenone (1.04 g, 4.26 mmol) and 4-(dimethylamino)pyridine (3.5 mg) in pyridine (0.73 mL) under dry nitrogen. The reaction mixture was stirred and allowed to warm slowly to 25° C. (about 45 min). The reaction was judged to be complete by tlc using silica gel thin layer plates and 20% (v/v) ethyl acetate in hexane as the mobile phase. The reaction mixture was poured onto ice and extracted with diethyl ether. The ether extract was washed with water and a saturated solution of NaHCO$_3$ in water, dried (MgSO$_4$) and concentrated under reduced pressure to give the title compound (961 mg, 100% yield). A small sample, purified by sublimation (30°-34° C., 0.05 mm), had mp 83°-84° C.; nmr (CDCl$_3$) δ 2.65 (s, 3H), 7.1 (d, J=9 Hz, 1H), 7.25 (m, 1H), 7.35 (q, J=8 Hz, 1H), 7.85 (m, 1H), 8.05 (d, J=9 Hz, 1H); uvλmax (MeOH) 335 nm (ε 2,770), 322 (2,420), 293 (4,050), 281 (4,680), 222 (46,400); Anal Calcd for C$_{12}$H$_9$F$_3$O: C, 63.72% H, 4,01%; Found: C, 63.47% H, 3.96%.

EXAMPLE 7

2-Methoxy-5-methyl-1-(trifluoromethyl)naphthalene (VII, R=CH$_3$)

Dimethylsulfate (1.13 g, 8.75 mmol, 0.85 mL) was added to a stirred suspension of 5-methyl-1-(trifluoromethyl)-2-naphthalenol (1.8 g, 7.96 mmol) and potassium carbonate (2.2 g, 15.9 mmol) in dimethylformamide (20 mL). After stirring the reaction mixture for 2 hr at 25° C. the solid in the reaction mixture was removed by filtration. The filtrate was extracted with hexane (400 mL). The extract was washed with brine, dried (MgSO$_4$) and concentrated to dryness giving 1.7 g (90% yield) of the title compound. This product was used for the reaction described in the next example. A sample of the product, recrystallized from hexane, had mp 70°-71° C.; nmr (CDCl$_3$) 67 2.65 (s, 3H), 3.95 (s, 3H), 7.2 (m, 2H), 7.35 (q, J=8 Hz, 1H), 8.0 (m, 1H), 8.1 (d, J=9 Hz, 1H); ir (CHCl$_3$) 1390, 1340, 1280, 1255, 1245, 1110, 1095, 1085, 1045 cm$^{-1}$; uvλmax (MeOH) 336 nm (ε 2,910), 323 (2,645), 297 (4,440), 286 (4,880), 236 (30,050), 224 (46,730).

EXAMPLE 8

6-Methoxy-5-(trifluoromethyl)-1-naphthalenecarboxylic acid (VIII, R=CH$_3$)

Procedure A:

A solution of KMnO$_4$ (1.58 g, 10 mmol) in water (15 mL) was added dropwise over a period of 6 hr to a refluxing solution of 2-methoxy-5-methyl-1-(trifluoromethyl)naphthalene (500 mg, 2.1 mmol)in water/tert-butanol (11.8: 88.2; 10 mL). The mixture was heated at reflux for an additional one hour and, while still hot, the mixture was filtered. The solid, collected on the filter, was washed with hot water and ethyl acetate. The combined filtrate and washings were concentrated under reduced pressure to a volume of about 3 mL. Water (20 mL) and 0.5N aqueous NaOH (10 mL) were added to the residue. The mixture was extracted with diethyl ether. After drying (MgSO$_4$) and evaporating of the extract, 140 mg of starting material was obtained. The aqueous layer from the preceding extraction was rendered acidic with 1N aqueous H$_2$SO$_4$. The resulting precipitate was collected, washed on the filter with water and dried over P$_2$O$_5$ under reduced pressure for 18 hr to give the title compound (222 mg, 55% yield based on recovered starting material). The product had mp 221°-222° C.

Procedure B:

A suspension of 2-methoxy-5-methyl-1-(trifluoromethyl)naphthalene (1.2 g, 5.0 mmol), N-bromosuccinimide (1.07 g, 6.0 mmol) and benzoyl peroxide (20-30 mg) in carbon tetrachloride (10 mL) was heated at reflux for 1.5 hr. The residual solid in the reaction mixture was removed by filration, and the collected solid on the filter was washed with methylene chloride. The combined filtrates were washed with water, dried (MgSO$_4$) and evaporated to give 1.7 g of 5-(bromomethyl)-1-(trifluoromethyl)-2-methoxynaphthalene (IX, R=CH$_3$ and R$^1$=CH$_2$Br) which was used in the next step without purification. Crystallization of a sample from hexane furnished pure 5-(bromomethyl)-1-trifluoromethyl-2-methoxynaphthalene having mp 97°–99° C.; nmr (CDCl$_3$) δ 3.95 (s, 3H), 4.85 (s, 2H), 7.7 (m, 5H); ir (CHCl$_3$) 1265, 1125 cm$^{-1}$; uvλmax (MeOH) 339 nm (ε 3,510), 326 (3,280), 300 (7,230), 288 (7,150), 229 (44,150); Anal Calcd for C$_{13}$H$_{10}$BrF$_3$O: C, 48.93% H, 3.16%; Found: C, 48.88% H, 3.14%.

A stirred mixture of the latter compound (2.0 g, 5.25 mmol) and hexamethylenetetramine (1.76 g, 12.6 mmol) in acetic acid (2.6 mL) and water (2.6 mL) was heated at reflux for 3 hr. Concentrated HCl (2.6 mL, 38% w/v HCL in water) was added to the mixture, and the refluxing of the mixture was continued for 45 min. The mixture was extracted with toluene. The extract was washed successively with brine, aqueous NaHCO$_3$ solution and brine. Thereafter, the extract was dried (MgSO$_4$) and evaporated to dryness to give 1.5 g of 6-methoxy-5-(trifluoromethyl)-1-naphthalenecarboxaldehyde (X, R=CH$_3$ and R$^1$=CHO); mp 92°–94° C.; nmr (CDCl$_3$) δ 3.95 (s, 3H), 7.0-9.5 (m, 5H), 10.65 (s, 1H); ir (CHCl$_3$) 1690, 1260, 1150, 1100 cm$^{-1}$. The latter compound (1.5 g) was dissolved in hot tert-butanol/water (7:1, 30 mL). The solution was heated to reflux. Solid KMnO$_4$ (1.1 g, 7 mmol) was added in one portion to the fluxing solution. The mixture was refluxed for 45 min. Precipitated MnO$_2$ in the mixture was reduced by the addition of solid NaHSO$_3$. The mixture was evaporated to dryness. The residue was suspended in water. By the addition of concentrated HCl, the pH of the suspension was adjusted to about 3. The suspension was extracted with ethyl acetate. The ethyl acetate extract was washed with brine and then extracted with 0.5N aqueous NaOH (about 150 ml). The alkaline extract was made acidic with aqueous HCl. The resulting precipitate was collected and dried to give 1.12 g of the title compound, i.e. 80% yield from 5-(bromomethyl)-1-(trifluoromethyl)-2-methoxynaphthalene. This product was identical to the product obtained by procedure A of this example.

We claim:

1. A process for preparing 5-methyl-1-(trifluoromethyl)-2-naphthalenol, which comprises:
    aromatizing 3,4-dihydro-1-hydroxy-5-methyl-1-(trifluoromethyl)-2(1H)-naphthalenone with a dehydrating agent of the type capable of acylating tertiary alkanols and is one of thionyl bromide, thionyl chloride, phosphorus oxychloride, acetyl chloride, mesyl chloride or acetyl chloride in the presence of an organic proton acceptor, or trifluoroacetic anhydride or acetic anhydride.

2. 5-Methyl-1-(trifluoromethyl)-2-naphthalenol and its corresponding lower alkyl ethers.

3. 2-Methoxy-5-methyl-1-(trifluoromethyl)naphthalene, as claimed in claim 2.

* * * * *